United States Patent [19]

Kenny et al.

[11] Patent Number: 5,491,344

[45] Date of Patent: Feb. 13, 1996

[54] METHOD AND SYSTEM FOR EXAMINING THE COMPOSITION OF A FLUID OR SOLID SAMPLE USING FLUORESCENCE AND/OR ABSORPTION SPECTROSCOPY

[75] Inventors: Jonathan E. Kenny, Lexington, Mass.; Todd A. Taylor, Chittenden, Vt.

[73] Assignee: Tufts University, Medford, Mass.

[21] Appl. No.: 160,514

[22] Filed: Dec. 1, 1993

[51] Int. Cl.$^6$ .................................................. G01N 21/64
[52] U.S. Cl. ..................................... 250/461.1; 250/459.1
[58] Field of Search ............................. 250/461.1, 459.1; 356/317, 318

[56] References Cited

U.S. PATENT DOCUMENTS

| | | | |
|---|---|---|---|
| 4,916,319 | 4/1990 | Telfair et al. | 250/461.1 |
| 5,149,026 | 9/1992 | Fay et al. | 250/461.1 |
| 5,274,240 | 12/1993 | Mathies et al. | 250/461.1 |
| 5,303,026 | 4/1994 | Strobl et al. | 250/318 |
| 5,304,492 | 4/1994 | Klinkhammer | 250/461.1 |

OTHER PUBLICATIONS

Johnson et al., "Video fluorometer," Rev. Sci. Instrum., vol. 50(1), pp. 118–126 (Jan. 1979).
Hershberger et al., "Sub–Microliter Flow–Through Cuvette for Fluorescence Monitoring of High Performance Liquid Chromatographic Effluents," Analytical Chemistry, vol. 51, No. 9, pp. 1444–1446 (Aug. 1979).
Nir et al., "CCD detectors record multiple spectra simultaneously," Laser Focus World, pp. 111–120 (Aug. 1991).
Hershberger et al., "Liquid Chromatography with Real–Time Video Fluorometric Monitoring of Effluents," Anal. Chem., vol. 53, pp. 971–975 (1981).
Skoropinski et al., "Laser Videofluorometer System for Real–Time Characterization of High–Peformance Liquid Chromatographic Eluate," Anal. Chem., vol. 58, pp. 2831–2839 (1986).

Primary Examiner—Davis L. Willis
Assistant Examiner—Richard Hanig
Attorney, Agent, or Firm—Kriegsman & Kriegsman

[57] ABSTRACT

A method and system for examining the composition of a fluid or solid sample using fluorescence and/or absorption spectroscopy. In one embodiment, the system is adapted for use in examining liquid effluents as they elute from the end of a liquid chromatography column and comprises a Nd:YAG laser coupled to a harmonic generator. Pulses of the fourth harmonic therefrom are focused into a Raman shifter filled with a mixture of hydrogen and methane gases. The laser pulses have an intensity sufficient to produce an array of different-colored laser pulses by stimulated Raman scattering within the Raman shifter. These different-colored pulses are then dispersed according to their respective wavelengths and then launched into a plurality of optical fibers. The fibers tranmit the different-colored pulses to a specially-designed detection cell, where they simultaneously excite a flowing fluid sample contained within the cell at the same point of axial fluid flow. The fluid sample enters and exits the detection cell via tubes. Ultraviolet and visible lamp light is also used to illuminate the fluid sample, and the attenuation of this light is used to obtain an absorption spectrum of the sample. Optical fibers are used to transport fluorescent light, transmitted lamp light and a fraction of the Raman-shifted laser light to an imaging spectrograph. The light from each optical fiber is dispersed along a narrow strip by the spectrograph to produce an array of strips, each strip corresponding to one of the fibers, and is focused on the surface of a 2-dimensional CCD detector. The CCD detector converts each strip into electrical charges, which are digitized and processed by a computer to create an EEM. The aforementioned system is capable of obtaining an absorption spectrum from 200–479 nm with 0.5–5 nm spectral resolution and 10 fluorescence spectra simultaneously every 0.1–250 seconds for several hours, with crosstalk between channels of less than $10^{-4}$.

25 Claims, 11 Drawing Sheets

METHOD AND SYSTEM FOR EXAMINING THE COMPOSITION OF A FLUID OR SOLID SAMPLE USING FLUORESCENCE AND/OR ABSORPTION SPECTROSCOPY

BACKGROUND OF THE INVENTION

The present invention relates generally to methods and systems for examining the composition of a fluid or solid sample and more particularly to methods and systems for examining the composition of a fluid or solid sample using optical spectroscopy.

With the advent and ever-increasing use of High-Performance Liquid Chromatography (HPLC) in the chemical and biotechnology arts, the need for instrumentation capable of quickly and accurately analyzing the composition of HPLC effluent samples has heightened.

In *Rev. Sci. Instrum.*, Vol. 50, No. 1, pp. 118–126 (Jan. 1979), Johnson et al. disclose a video fluorometer - a rapid scanning fluorescence system which uses a particular method of sample illumination and a two dimensional multichannel detector (SIT vidicon detector) to acquire fluorescence excitation and emission spectra simultaneously. More specifically, the Johnson video fluorometer comprises a xenon arc lamp, the output of which is focused onto the entrance slit of a quarter meter Ebert type monochromator equipped with interchangeable 295 1/mm gratings blazed at 250 and 400 nm. The monochromator is turned on its side so that the long axis of the entrance slit is perpendicular to the long axis of a cuvette holding a fluid sample. The exit slit and the slit holder have been removed; therefore, emerging at the exit slit plane is a 2-cm vertically dispersed polychromatic beam of radiation spanning 260 nm which is focused at 1:1 magnification onto the center of the sample cuvette. At 90 degrees to the excitation beam, the fluorescent image in the cuvette is focused at 1:1 magnification onto the entrance slit of an analyzing monochromator, which is oriented in the usual fashion with the long axis of the slit parallel to the long axis of the cuvette. Again, the exit slit and the slit holder have been removed; this results in a two dimensional image at the exit plane. The image may be represented as an Emission Excitation Matrix (EEM) whose matrix elements $M_{ij}$ represent the fluorescence intensity excited by wavelength i and observed at wavelength j. The EEM image is subsequently focused with 2:1 demagnification onto the target of a multichannel imaging detector.

In Analytical Chemistry, Vol. 51, No. 9, pp. 1444–1446 (Aug. 1979), Hershberger et al. disclose a sub-microliter flow-through cuvette suitable for monitoring liquid chromatographic effluents. The cuvette is based on the sheath flow principle, in which the chromatographic effluent is injected into the center of an ensheathing solvent stream but does not mix with it because laminar flow conditions are maintained. The optical volume of the cuvette is varied by adjusting the relative flow rates of sheath and sample. The response of the flow cell to a chromatographic effluent was obtained using a system comprising a laser for providing excitation radiation of one wavelength, a focusing lens for focusing the laser radiation onto the flow cell, a photomultiplier tube for measuring fluorescence intensity and a microscope for collecting the fluorescent light from the cuvette and for focusing it on the photomultiplier tube.

In *Anal. Chem.*, Vol. 53, pp. 971–975 (1981), Hershberger et al. disclose using the above-described Johnson video fluorometer to examine effluents obtained by High-Performance Liquid Chromatography through a modified Hershberger laminar flow cell.

In *Anal. Chem.*, Vol. 58, pp. 2831–2839 (1986), Skoropinski et al. disclose a laser videofluorometer system for real-time characterization of High-Performance Liquid Chromatographic eluate. The instrument comprises a nitrogen-laser-pumped dye laser as the excitation source and a quarter meter polychromator/microchannel plate-intensified diode array as the fluorescence detector. The dye laser cavity is tuned with a moving-iron galvanometer scanner grating drive, permitting the laser output to be changed to any wavelength in its range in less than 40 ms.

The present inventors have identified the following shortcomings in the above-described prior art systems which use a white light lamp as the excitation source: (1) The lamps typically do not excite strongly in the far UV region of the spectrum (i.e. approximately 220–300 nm) where most fluorescent compounds absorb light strongly; (2) Dispersion of lamp light is typically effected using multiple grating orders, which often result in interfering light; (3) Bandwidth inaccuracies sometimes occur due to large excitation spectral bandwidths; (4) The associated detector frequently has high interchannel crosstalk; (5) In many instances, an intensifier is located between the spectrograph and the CCD camera of the detection system, which degrades spectral resolution and/or increases interchannel crosstalk; (6) The emission spectral resolution is not always constant for all spectra of the EEM across the complete wavelength range of each spectrum; (7) Both absorption spectra and fluorescence EEM's cannot be obtained for the same sample; and (8) The spectra for the EEM's are obtained along the axis of the liquid flow; therefore, when the system is used in series with HPLC, each spectrum of a given EEM arises from a solution having a different chemical composition from its neighboring spectra.

In addition, the present inventors have identified the following shortcomings in the above-described prior art systems which use laser light as an excitation source: (1) The laser source can only generate laser beams over short wavelength ranges (30–70 nm) of a region of the spectrum at one time; consequently, the operator must intervene to change from one wavelength range to another; (2) The excitation spectral resolution is only about 2 nm; (3) Only one wavelength of laser light is generated at a time, and only one fluorescence spectrum is detected at one time; consequently, when used in series with HPLC, sequentially obtained spectra may correspond to samples of different chemical compositions; and (4) Moving parts are required to change the excitation wavelength.

Additional publications of interest include Nir et al., *Laser Focus World*, pp. 111–120 (Aug. 1991).

SUMMARY OF THE INVENTION

It is an object of the present invention to provide a novel method and system for examining the composition of a fluid or solid sample.

It is another object of the present invention to provide a method and system as described above which overcomes at least some of the shortcomings associated with the methods and systems of the prior art.

It is still another object of the present invention to provide a method and system as described above which can either be used in conjunction with HPLC, to examine the composition of a chromatographic effluent, or can be used independently of HPLC, in other flow systems or as a general purpose chemical detector.

According to one feature of the present invention, laser light of many different wavelengths may be used to simultaneously excite an effluent sample along the same position of fluid flow so that all of the spectra used to generate an EEM may be obtained from a sample of the same chemical composition.

According to another feature of the present invention, both absorption spectra and fluorescence spectra may be obtained from the same sample.

In furtherance of the objects and features set forth above, the present invention comprises, for example, in a preferred embodiment a Nd:YAG laser, a harmonic generator for generating a family of harmonics based on the Nd:YAG laser output, a Pellin-Broca prism for dispersing (i.e. separating) the harmonics based on their respective wavelengths, optics for focusing the fourth harmonic (i.e. 266 nm) into a Raman shifter, a Raman shifter for using the fourth harmonic to generate Raman shifted light of a plurality of wavelengths, optics for collimating the output of the Raman shifter, a second Pellin-Broca prism for dispersing the output of the Raman shifter along a plurality of paths, each path being traversed by light of a particular wavelength, a first plurality of optic fibers, each optic fiber of said first plurality being disposed along one of the paths and being used to transmit Raman shifted light of a specific wavelength, a fluid detection cell for holding a sample effluent, means for delivering and removing effluents to and from said fluid detection cell, a second plurality of optic fibers, each one of said second plurality of optic fibers being arranged to transmit from the fluid detection cell fluorescence from the sample effluent resulting from the excitation of light transmitted by one of the optic fibers from said first plurality of optic fibers, a lamp source for illuminating the sample effluent in said fluid detection cell with white light suitable for absorption measurements, a third plurality of optic fibers arranged to receive the white light transmitted through the sample effluent in the fluid detection cell, an imaging spectrograph for resolving the output from each optic fiber of said second and third pluralities of optic fibers, a 2-dimensional CCD detector for reading the output of the imaging spectrograph, a computer for processing the output of the CCD detector into EEM's and absorption spectra and display means for displaying the EEM's and absorption spectra.

Some of the positive attributes associated with the embodiment described above are that the laser wavelengths and laser wavelength bandwidths are always known exactly, never change over time, and no part of the excitation or detection arrangement involves the use of moving parts during data collection or needs regular instrumental calibration or maintenance. The detection arrangement can be calibrated very rapidly and accurately using the excitation laser light. Thus, the entire system is rugged, cheap to maintain and capable of acquiring spectral databases that will be extremely precise and accurate over time (i.e. hundreds of years).

In addition, the above-described system uses high-intensity short-pulse-duration laser beams for fluorescence excitation. By using pulsed light (in combination with a gated detector), the differentiation of chemicals based on their fluorescence lifetimes is permitted.

Furthermore, by integrating fiber optics into a fluorescence EEM parallel spectroscopy flow detector system of the type described above, the following are made possible: fluorescence optical alignment independent of absorption optical alignment; free movement of many components of the detection arrangement and the fluid detection cell without affecting optical alignments; the convenience of coupling different optical information channels (absorption, fluorescence, scattering and power normalization) originating from different parts of the system into the same detector for chromatic analysis; and the ability to interchange different types of sample holders for analyzing different types of solid and liquid samples.

Additional objects, features and advantages of the invention will be set forth in part in the description which follows, and in part will be obvious from the description or may be learned by practice of the invention. The objects of the invention also may be realized and attained by means of instrumentalities and combinations not particularly pointed out in the description which follows but set forth in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In the drawings wherein like reference numerals represent like pans.

DETAILED DESCRIPTION OF PREFERRED EMBODIMENTS

Figure 1:
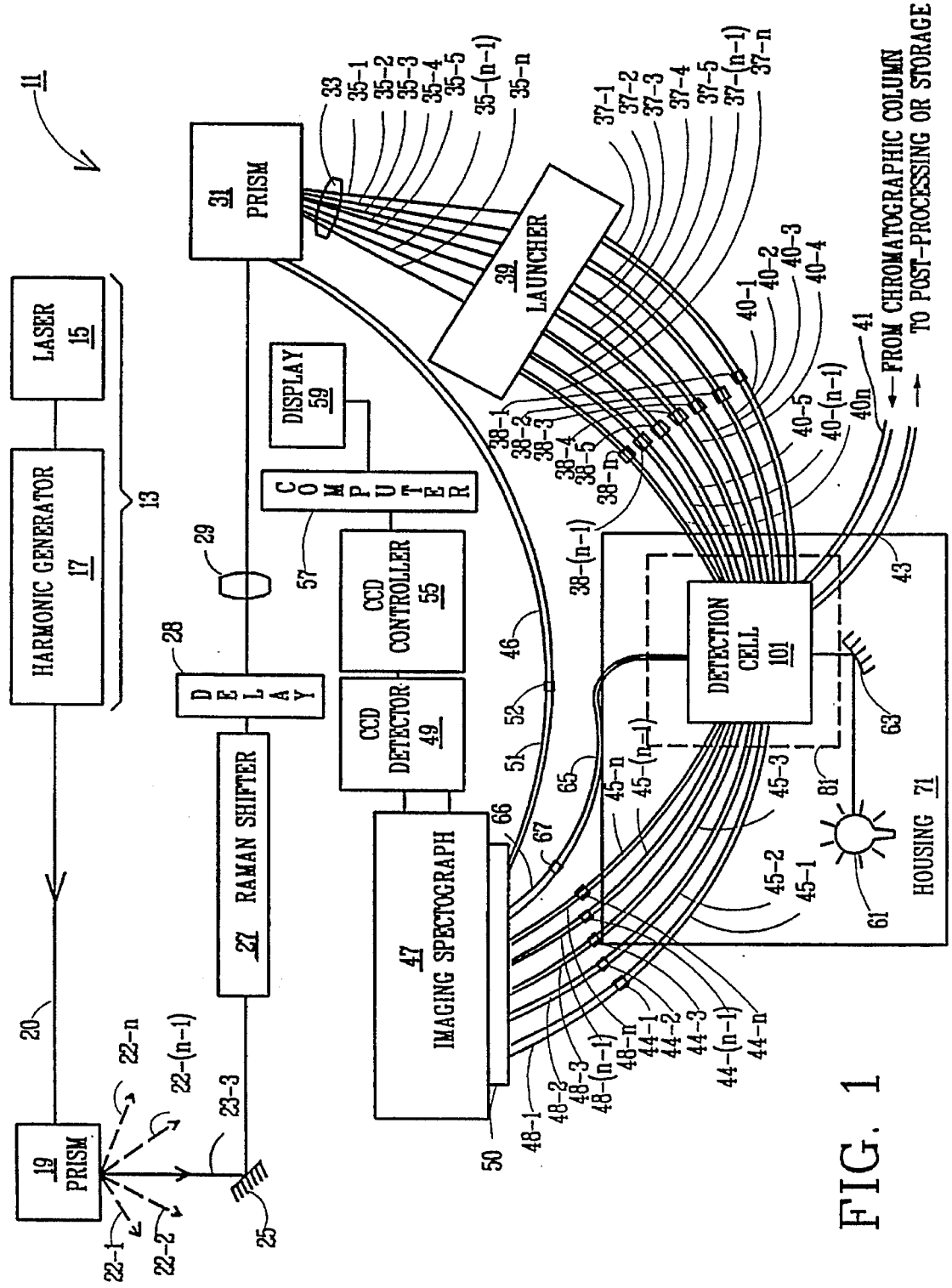
FIG. 1 is a part schematic, part block diagram of one embodiment of a system for examining the composition of a fluid sample using fluorescence and/or absorption spectroscopy, the system being constructed according to the teachings of the present invention.

Referring now to FIG. 1, there is shown a part schematic, part block diagram of a system for examining the composition of a fluid sample according to the teachings of the present invention, the system being represented by reference numeral 11.

System 11 comprises a pulsing laser source 13. Pulsing laser source 13 includes a pulsing laser 15 and a harmonic generator 17, harmonic generator 17 being coupled to the output of laser 15. The combined output of laser 15 and harmonic generator 17 must be capable of providing enough UV radiation, preferably in the 200–280 nm spectral range, to pump the Raman shifter to be described below. Optimum pump conditions require that the laser intensity be above the threshold for stimulated Raman scattering and be close to the intensity required for decomposition of the fluid contained in the Raman shifter (which would be approximately 0.4–7 $GW/mm^2$ peak power at the cavity focal point for a Raman shifter containing hydrogen and methane gas). Preferably, the average pulse energy from laser source 13 is constant over time and its pulse-to-pulse energy variation is small. Examples of lasers suitable for use as laser 15 include flash lamp pumped or diode-pumped solid state lasers (e.g., Nd:YAG, Nd:YLF, Cr:LiSrAlF$_6$, or Ti:sapphire), gas lasers (excimer, metal vapor or nitrogen), cw diode lasers and their harmonics, dye lasers and ultrafast picosecond and femtosecond lasers. Preferably, laser 15 is a Nd:YAG laser, its fourth harmonic being a 266 nm pulsed beam.

System 11 also includes a Pellin-Broca prism 19 or the like (e.g. a grating) for use in dispersing the multichromatic pulses 20 emitted from laser source 13 along a plurality of angularly diverging paths 22-1 through 22-n based on their constituent wavelengths. In this manner, light of a particular desired wavelength may be selected and separated from the remaining light of its respective pulse. Preferably, the selected light is in the deep UV spectral region, and where laser 15 is a Nd:YAG laser, the selected light is preferably the fourth harmonic, i.e. 266 nm, which travels along path 22-3. These pulses of light are then reflected off and are focused by a mirror 25 (or a prism and lens combination) into a Raman shifter 27, which, by stimulated Raman scattering and four-wave mixing processes, converts each of the monochromatic pulses of light incident thereon into a corresponding multichromatic pulse of light.

Several different types of Raman shifter configurations may be used in shifter 27, such as direct-pump (single wavelength), direct pump (multiple wavelength), oscillator, or capillary waveguide configurations. In addition, several different types of gases at different pressures may be used in shifter 27. For example, a mixture of hydrogen and methane gases could be and was used because these gases are transparent in the ultraviolet region of the spectrum and because they have large cross sections for stimulated Raman scattering. The ratio of the hydrogen and methane gases in shifter 27 was chosen so that the observed laser intensities of the first stokes pulses of each gas emitted therefrom were approximately equal, and the pressure of the gas mixture was chosen to optimize the intensity of the anti-Stokes laser pulses. These conditions were found to provide the maximum number of different wavelength pulses emitted from shifter 27 and the highest beam intensities in the far-UV region of the spectrum.

System 11 also includes an optical fiber delay unit 28 through which light pulses emitted from Raman shifter 27 are passed. Unit 28, which converts each light pulse transmitted therethrough into a train of lower intensity pulses, includes a bundle of UV-transmitting optical fibers of various integer lengths to the length of the light pulse emitted from Raman shifter 27. For example, if each pulse of light emitted from shifter 27 is 1 meter in length (~4 ns duration) and it was desired to break this pulse into 3 pulses each having ~⅓ of the original pulse's intensity, one third of the optical fibers would be 1 meter long, one third would be 2 meters long, and one third would be 3 meters long. These different-length fibers are randomly arranged or consecutively alternated and preferably have small core (<100μm diameter) and cladding (<10μm thickness) sizes with respect to the laser beam diameter. The fibers are looped around so that all fiber ends are flush at surface where the beams are launched into the unit and where the beams emerge from the unit. The fibers are stripped at their ends and are either tightly wrapped together so that the cladding of each fiber is touching the cladding of its adjacent fibers or the fibers are fused together at the ends. By convening each high-intensity pulse from Raman shifter 27 into several lower-intensity pulses, more total light can be focused into optical fibers 37-1 to 37-n (to be discussed further below) without damaging the fibers. Unit 28 could include other numbers or lengths of optical fibers to reduce the high-intensity pulses from shifter 27 into lower-intensity pulses. This unit could be designed so that some of the light pulse from Raman shifter 27 passes around the sides of unit 28 and goes directly onward without passing through unit 28.

System 11 additionally comprises a lens 29 for focusing the light pulses emitted from shifter 27 into a prism 31. Prism 31 disperses the focused light according to its constituent wavelengths. A lens (or lenses) 33 is then used to focus the dispersed light along a plurality of angularly divergent paths 35-1 through 35-n (n typically being about 40 where the fourth harmonic of a Nd:YAG laser is shifted by the above-described hydrogen/methane Raman shifter). The pulses traveling along paths 35-1 through 35-n are then launched into a corresponding plurality of channels or optical fibers 37-1 through 37-n via a launcher 39. In this manner, each optical fiber 37 transmits light pulses of only one wavelength. Although not shown, launcher 39 comprises (1) a device to hold separate optical filters for each channel to allow reduction of any laser beam's intensity prior to launching the beam into its optical fiber 37 and (2) an optical rail, mounted on a multi-axis positioner, holding a movable stage for each optical fiber. Each stage can be independently translated along the rail, thereby allowing independent alignment of any optical fiber with any one focused laser beam.

The light pulses conducted by fibers 37-1 through 37-n are then transmitted into optical fibers 40-1 through 40-n through couplers 38-1 through 38-n. Couplers 38-1 through 38-n permit fibers 40-1 through 40-n to be disconnected from a fluid detection cell 101 (to be discussed in detal below) and reattached to any other detection cell or similar device without affecting the alignment of the laser beams with the launching optical fibers. The light pulses are transmitted through optical fibers 40-1 through 40-n to fluid detection cell 101 where the pulses are used simultaneously to excite a fluid sample contained within cell 101 at spatially discrete locations. Where, as in the case of the embodiment shown, system 11 is to be used as an "on-the-fly" detector for use with chromatographic techniques (such as HPLC), an input tube 41 is provided to conduct effluent samples from the chromatographic column to detection cell 101 and an output tube 43 is provided to conduct the tested samples to storage or to additional processing.

System 11 further comprises a second plurality of optic fibers 45-1 through 45-n. Fibers 45-1 through 45-n are arranged relative to fibers 40-1 through 40-n, respectively, so that each fiber 45 only receives the fluorescence emitted from the fluid sample within cell 101 as a result of excitation by the light transmitted by a corresponding fiber 40. The fluorescent light is then passed into fibers 48-1 through 48-n through couplers 44-1 through 44-n which become linearly aligned in a spectrograph plug 50. Small optical filters (not shown) can be mounted over the ends of each fiber 48 where the fibers emerge from plug 50 to prevent undesired wavelength regions of light (e.g. scattered laser light) from entering a spectrograph 47 to be described below.

The fluorescent light transmitted through each fiber 48 (as well as a small fraction of the radiation of all the pulses for use as an intensity reference transmitted by a fiber 51 coupled through a coupler 52 to a fiber 46) is then spectrally resolved in imaging spectrometer 47. Signal dispersion must be accomplished with little interchannel crosstalk for system 11 to function effectively. The extent of crosstalk rejection is an important factor in determining the number of independent channels of information that can be acquired simultaneously. Flat-field imaging spectrographs are currently available that achieve image-specific flat-field dispersion by employing toroidal mirror optics, toroidal lens optics, and holographic-based image-specific dispersion. Detection at longer wavelengths or over a different wavelength range can be accomplished by rotating or changing the grating in the imaging spectrograph.

The output of imaging spectrometer 47 is then read by a charge coupled device (CCD) detector 49 and converted into electrical signals which are transmitted to a CCD controller 55. These signals are then processed by a computer 57 and shown on a display 59. Instead of using a CCD detector 49, any other type of 2-dimensional detector may be employed, such a charge injection device (CID), several diode array detectors, or position-sensitive photo-multiplier tubes (PMT's). Such detectors may either be cooled or intensified to achieve a high dynamic range. The active area and pixel size of the 2-dimensional detector may be of any size or variety.

System 11 further comprises a lamp source 61 for providing UV and visible light (approximately 200–470 nm) for absorption spectral analysis of the fluid sample contained in cell 101. Lamp source 61 preferably comprises an arrangement of deuterium, xenon and/or tungsten filament lamps (or the flash lamp of laser 15 transmitted by an optical fiber). The light emitted from lamp source 61 is reflected off and is focused by a focusing mirror 63 onto the fluid sample in cell 101. An optic fiber (or fibers) 65 coupled to an optic fiber (or fibers) 66 through a coupler 67 is used to convey the light transmitted through cell 101 to imaging spectrograph 47 for analysis in the same manner as described above for the analysis of fluorescent light. As can be seen, lamp source 61, mirror 63 and detection cell 101 are all enclosed within a housing 71.

As can readily be appreciated, in addition to providing the light necessary for the absorption measurements, lamp 61 could also be used, instead of the laser/Raman shifter/prism system described above, to provide the necessary excitation light for the fluorescence measurements, the output of lamp 61 being dispersed by a spectrograph or similar means.

Figure 2:
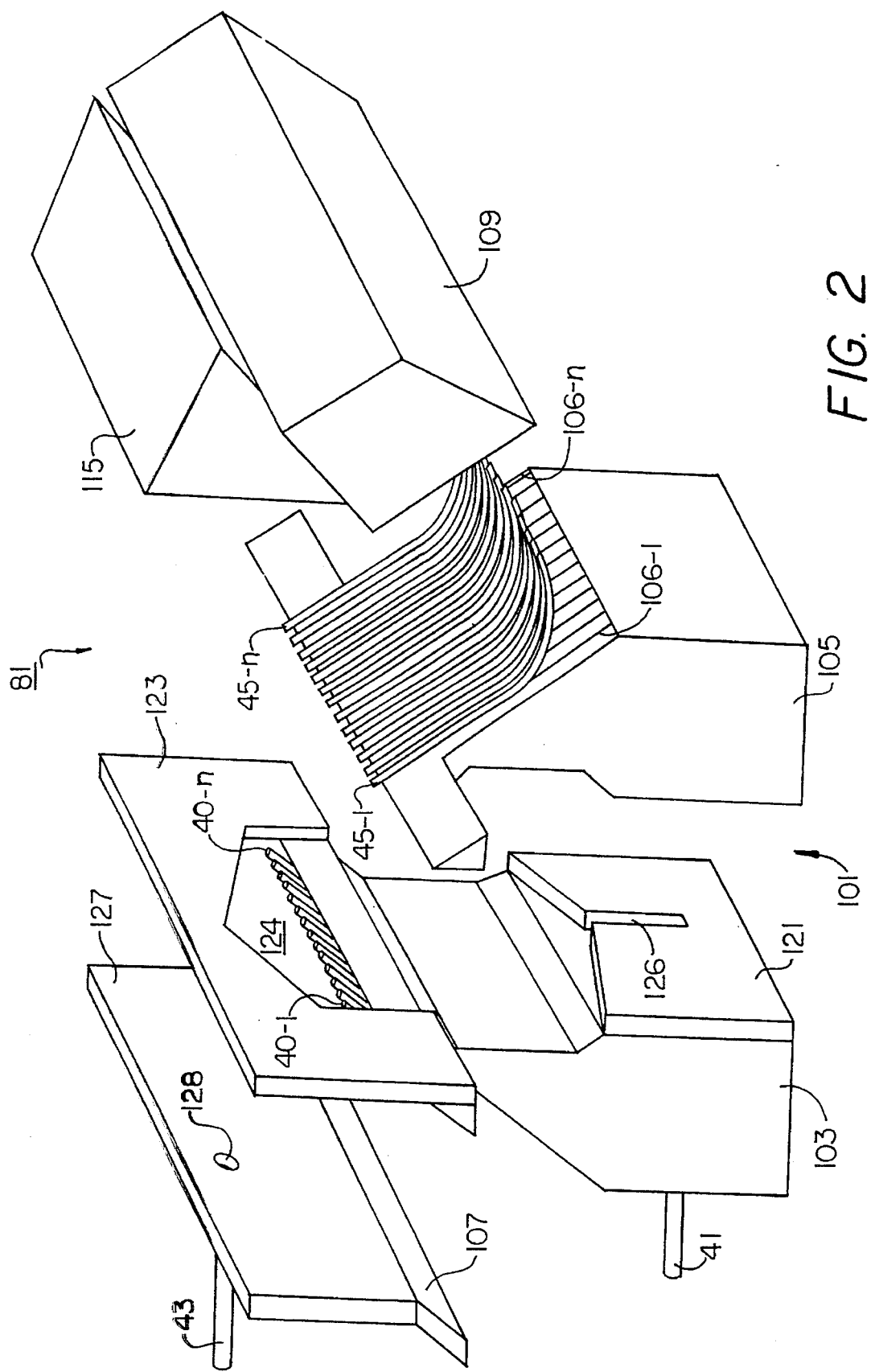
FIG. 2 is a partially exploded simplified perspective view of a portion of the system shown in FIG. 1 and represented therein by reference numeral 81.
Figure 4:
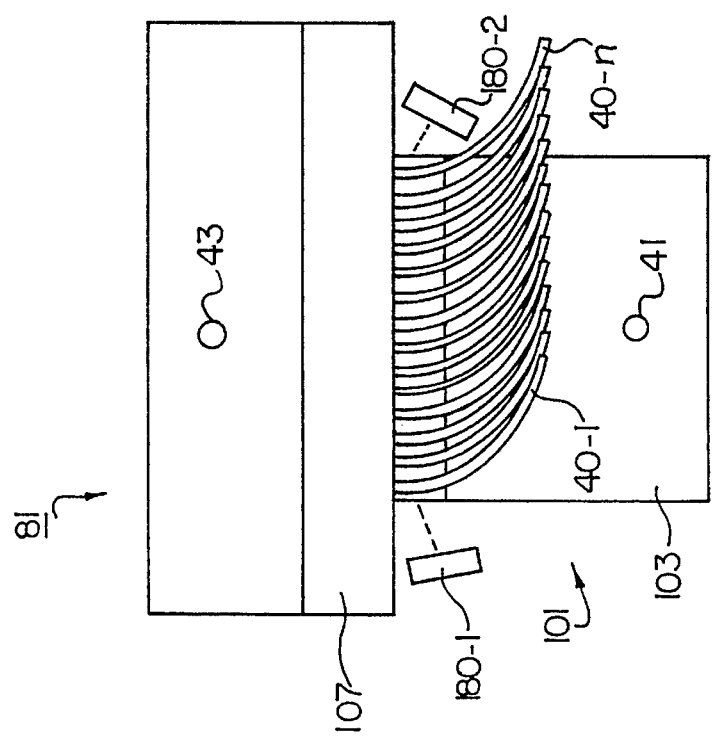
FIG. 4 is a partially exploded simplified front view of portion 81.
Figure 3:
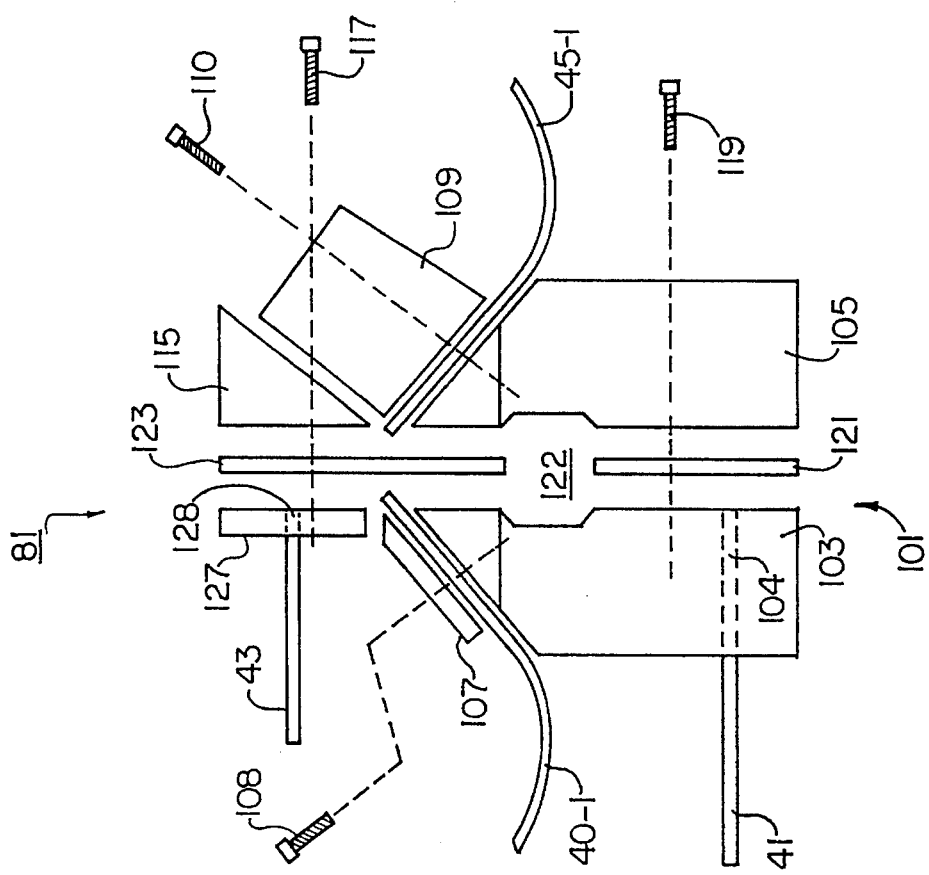
FIG. 3 is a partially exploded simplified side view of portion 81.

Referring now to FIGS. 2 through 4, there are shown a partially exploded simplified perspective view, a partially exploded simplified side view and a partially exploded simplified front view, respectively, of that portion of system 11 that is represented by reference numeral 81 in FIG. 1. As can be seen, portion 81 includes detection cell 101, fibers 37-1 through 37-n, fibers 45-1 through 45-n, input tube 41 and output tube 43.

Detection cell 101 comprises a left section 103 and a right section 105. Left section 103 is provided with a channel 104 through which fluid from inlet tube 41 enters. In addition, left section 103 is provided with a plurality of grooves (not shown) used to position fibers 40-1 through 40-n thereon, and right section 105 is provided with a corresponding plurality of grooves 106-1 through 106-n used to position fibers 45-1 through 45-n thereon. Fibers 40-1 through 40-n are held in place within the grooves on left section 103 by a left plate 107 secured to the top of left section 103 by a screw 108 (see FIG. 3). Fibers 45-1 through 45-n are held in place within grooves 106-1 through 106-n on right section 105 by a right block 109 secured to the top of right section 105 by a screw 110 (see FIG. 3).

A light sink prism 115, which has been partially painted black and which is used to absorb stray laser light from fibers 40-1 through 40-n, is mounted on top of right block 109 by a screw 117 (see FIG. 3).

Left section 103 and right section 105, which are coupled together by a pair of screws 119 (only one of which is shown in FIG. 3), are separated by a lower Teflon spacer 121 and an upper Teflon spacer 123. A pair of glass or silica windows 180-1 and 180-2 (see FIG. 4) interconnect the ends of sections 103 and 105 between spacers 121 and 123 to form a lower chamber 122 (see FIG. 3) for use in performing absorption measurements of the fluid sample. Spacer 123, in combination with prism 115 and a left upper plate 127, forms an upper chamber 124 (see FIG. 2) for use in performing fluorescence measurements of the fluid sample. Lower Teflon spacer 121 is provided with a slot 126 which serves to direct fluid from tube 41 upwardly between sections 103 and 105, first through lower chamber 122, then through upper chamber 124 and finally out through output tube 43 via a channel 128 formed in plate 124.

As can readily be appreciated, one advantage of the above-described detection cell and system is that all fluorescence measurements are taken at the same time and at the same point of axial fluid flow. Accordingly, the composition of the fluid sample tested remains constant for each series of fluorescence measurements.

One should recognize that, because fibers 40-1 through 40-n and 45-1 through 45-n can be disconnected from fibers 37-1 through 37-n and fibers 48-1 through 48-n, respectively, assemblies comprising alternative types of fluid detection cells may be interchanged with portion 81 for use with the remainder of system 11.

Figure 5:
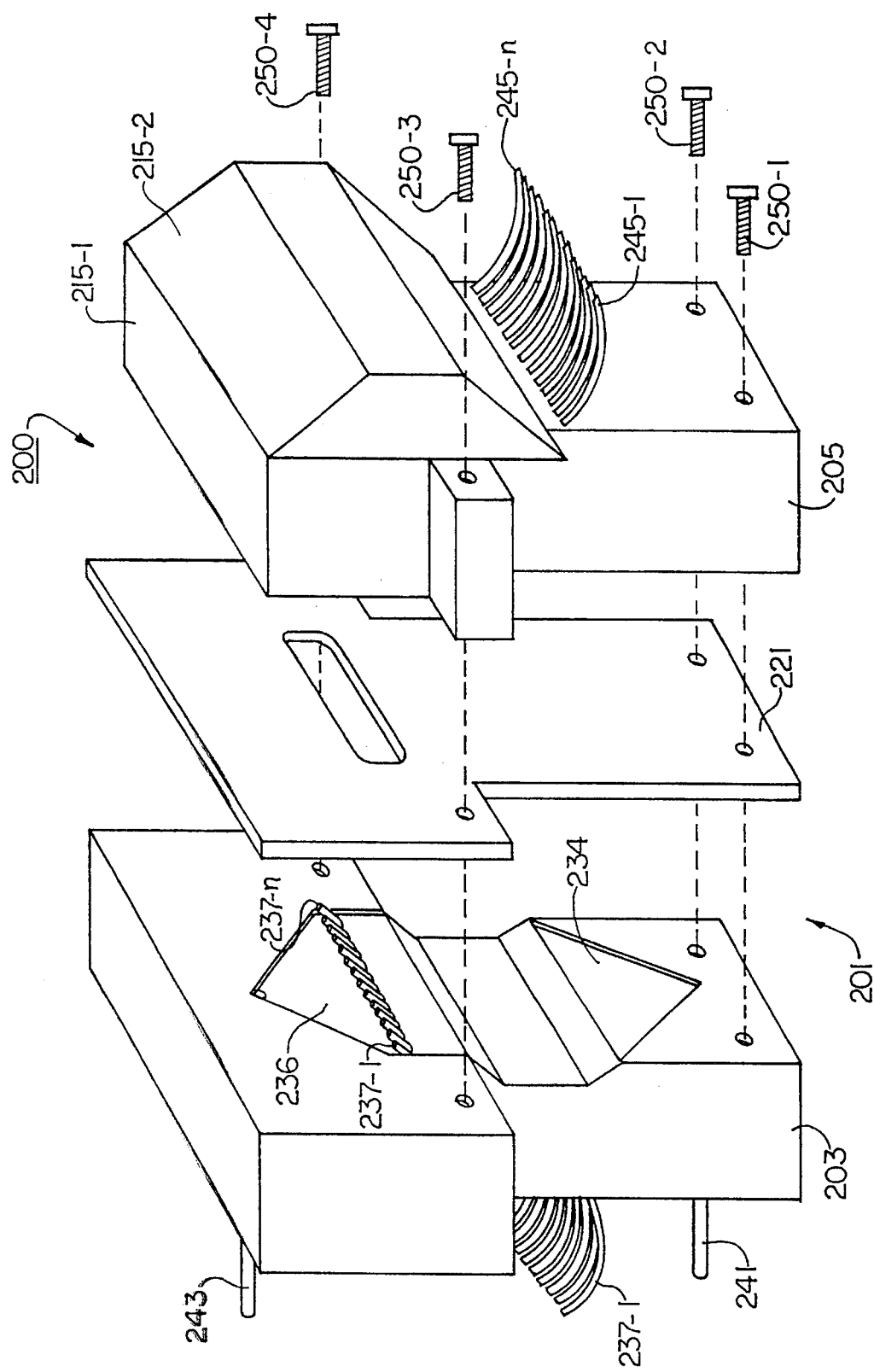
FIG. 5 is a partially exploded simplified perspective view of a first alternative assembly interchangeable with portion 81 for use with the remainder of the system of FIG. 1.

Referring now to FIG. 5, there is shown a partially exploded simplified perspective view of one such assembly interchangeable with portion 81 for use with system 11, the assembly being represented generally by reference numeral 200.

Assembly 200 comprises a detection cell 201, cell 201 including a left section 203, a right section 205, a pair of prisms 215-1 and 215-2, a spacer 221 and a pair of absorption cell windows (not shown). As can be seen, cell 201 is generally similar in construction and shape to cell 101, the primary differences being that (1) left section 103, left plate 107 and left upper plate 127 of cell 101 are integrally formed in cell 201 to form left section 203, (2) right section 105 and right block 109 of cell 101 are integrally formed in cell 201 to form right section 205, and (3) spacers 121 and 123 of cell 101 are integrally formed in cell 201 to form spacer 221. In addition, fluid transported to and from cell 201 using tubes 241 and 243, respectively, is directed through the interior of cell 201 by guides 234 and 236 milled into the inside face of section 203. Section 203 is provided with an array of channels (not shown) through which fibers 237-1 through 237-n are inserted. Fibers 237-1 through 237-n, which are connectable to fibers 37-1 through 37-n through couplers 38-1 through 38-n, respectively, function in an analogous manner to fibers 40-1 through 40-n of portion 81. In a manner similar to section 203, section 205 is provided with an array of channels (not shown) through which fibers 245-1 through 245-n are inserted. Fibers 245-1 through 245-n, which are connectable to fibers 48-1 through 48-n through couplers 44-1 through 44-n, respectively, function in an analogous manner to fibers 45-1 through 45-n of portion 81.

As can readily be appreciated, assembly 200 has fewer parts, is easier to machine, and is easier to assembly than portion 81. Proper positioning of optical fibers 237-1 through 237-n and 245-1 through 245-n is accomplished by inserting teflon spacer 221 between sections 203 and 205 after fibers 237 and 245 have been inserted thereinto. Such an arrangement insures that all fibers will align properly in the final assembly step when sections 203 and 205 are joined together using screws 250-1 through 250-4. A small amount of solvent-resistent epoxy is preferably used to seal in place optical fibers 237-1 through 237-n, optical fibers 245-1 through 245-n, prisms 215-1 and 215-2, and a pair of absorption cell windows (not shown). Alternatively, 0-ring slots could be milled into sections 203 and 205 to eliminate the need for epoxy.

Figures 6A, 6B:
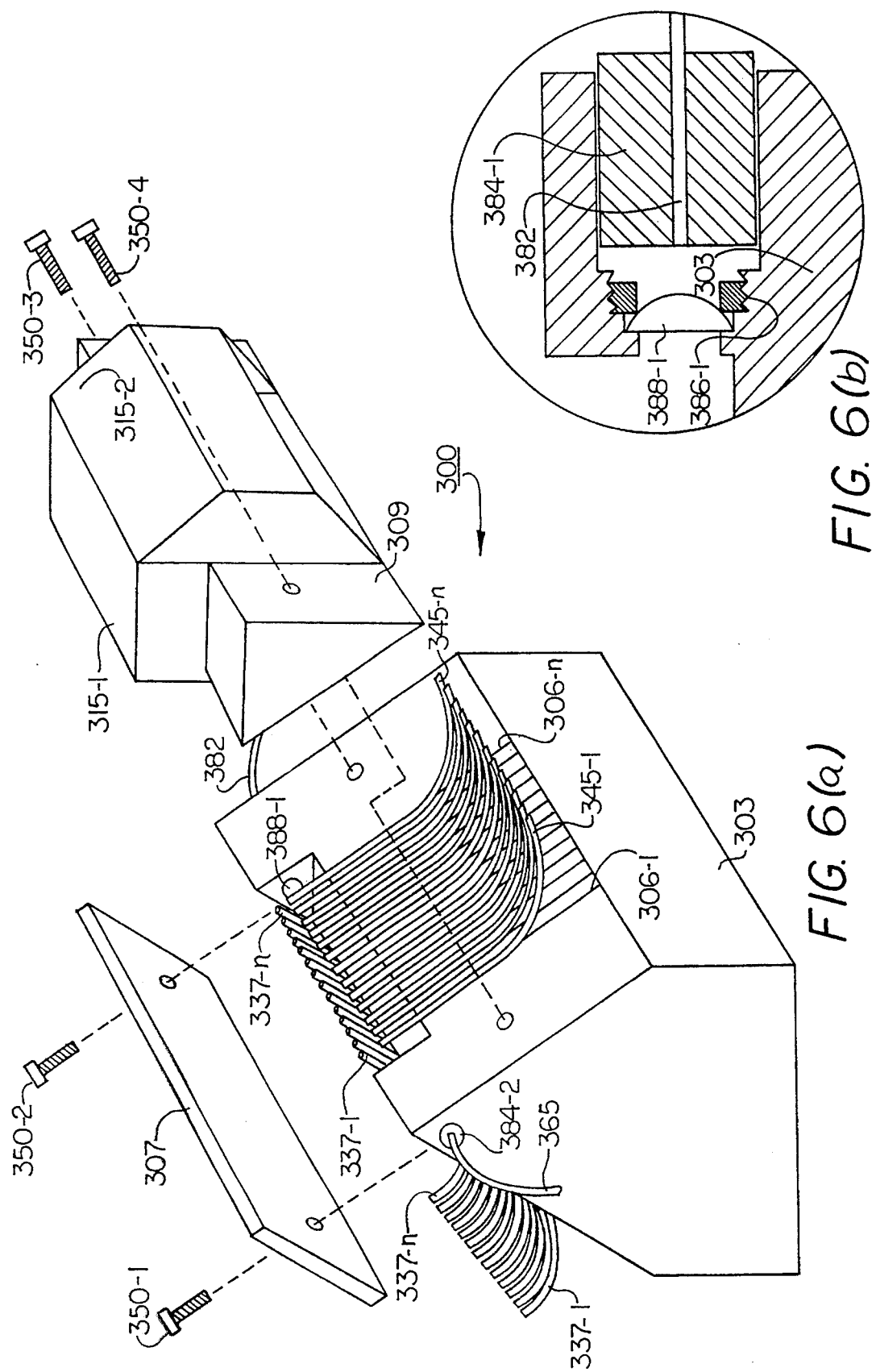
FIGS. 6(a) and 6(b) are partially exploded simplified perspective and enlarged fragmentary schematic section views, respectively, of a second alternative assembly interchangeable with portion 81 for use with the remainder of the system of FIG. 1.

Referring now to FIGS. 6(*a*) and 6(*b*), there are shown partially exploded simplified perspective and enlarged fragmentary schematic section views, respectively, of a second assembly interchangeable with portion 81 for use with system 11, the assembly being represented generally by reference numeral 300.

Assembly 300, which is specifically designed to be dipped directly into a solution for use in obtaining rapid absorption/fluorescence EEM data of the solution, comprises a support block 303. Support block 303 has a plurality of slots (not shown) formed on one surface thereof which are used to position a corresponding plurality of optical fibers 337-1 through 337-n. Fibers 337-1 through 337-n, which are connectable to fibers 37-1 through 37-n through couplers 38-1 through 38-n, respectively, function in an analogous manner to fibers 40-1 through 40-n of portion 81. A second plurality of optical fibers 345-1 through 345-n are positioned in a second group of slots 306-1 through 306-n formed on another surface of support piece 303. Fibers 345-1 through 345-n, which are connectable to fibers 48-1 through 48-n through couplers 44-1 through 44-n, respectively, function in an analogous manner to fibers 45-1 through 45-n of portion 81. Fibers 345-1 through 345-n are arranged on block 303 so as to be aligned with fibers 337-1 through 337-n, respectively, and the respective pluralities of fibers are held in place on block 303 by a plate 307 using screws 350-1 and 350-2 and by a block 309 using screws 350-3 and 350-4. A pair of prisms 315-1 and 315-2 that have been coated with a black material on their respective outside surfaces are mounted on block 309 and are used to absorb stray excitation light from fibers 337-1 through 337-n.

Absorption measurements of the solution using assembly 300 are carried out using the arrangement more clearly shown in FIG. 6(*b*), FIG. 6(*b*) being a fragmentary section view taken along the longitudinal axis of the assembly shown in FIG. 6(*a*). Continuum white light from lamp 61 is transmitted to block 303 by a fiber 382, the end of which is mounted in a plug 384-1. The light emitted from fiber 382 is then collimated by a small lens or lens combination 388-1 held in place by a support ring 386-1. That light which is not absorbed by the solution is then collected by a similar lens/optical fiber arrangement located on the opposite end of block 303 and transmitted away by a fiber 365 mounted in a plug 384-2.

Figure 7:
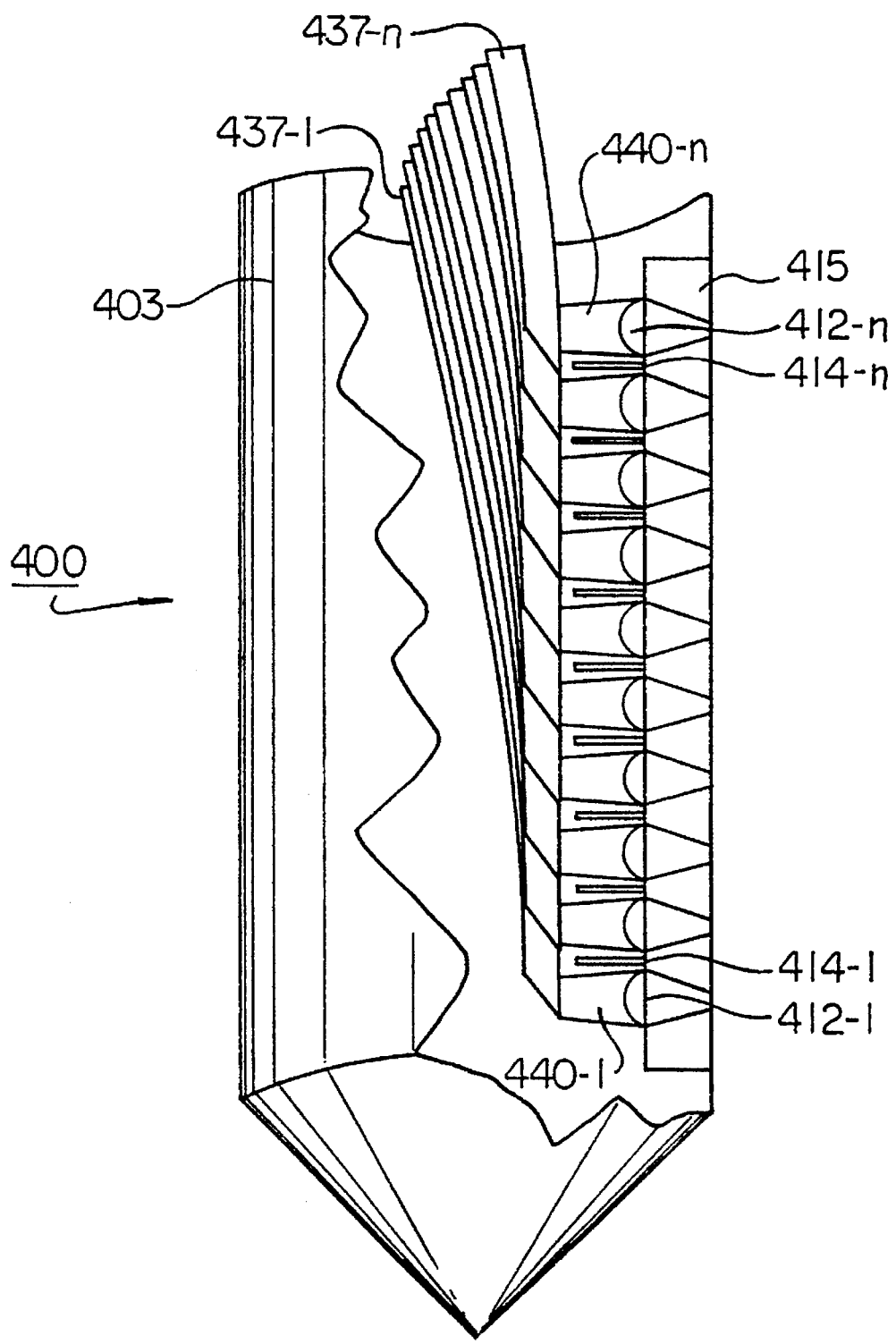
FIG. 7 is an enlarged fragmentary schematic section view of a third alternative assembly interchangeable with portion 81 for use with the remainder of the system of FIG. 1.
Figure 8A:
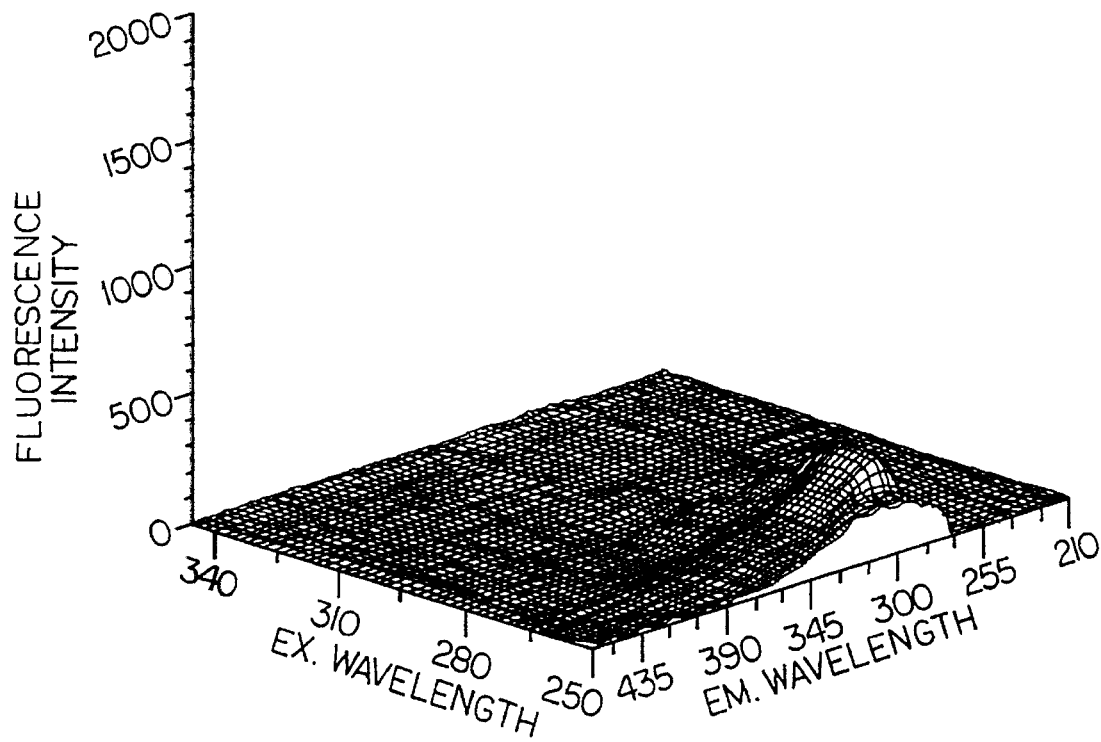
FIGS. 8(a) through 8(d) are EEM's for various pollutant mixtures obtained using the second alternative arrangement of FIGS. 6(a) and 6(b) with the remainder of the system of FIG. 1.
Figure 8B:
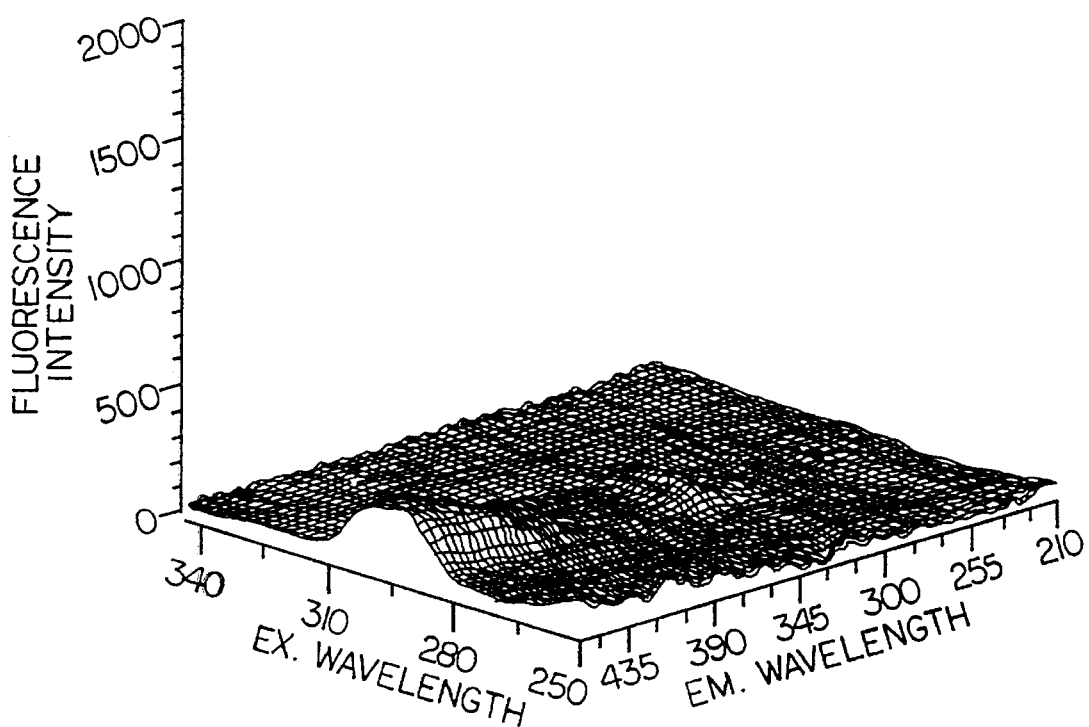
Figure 8C:
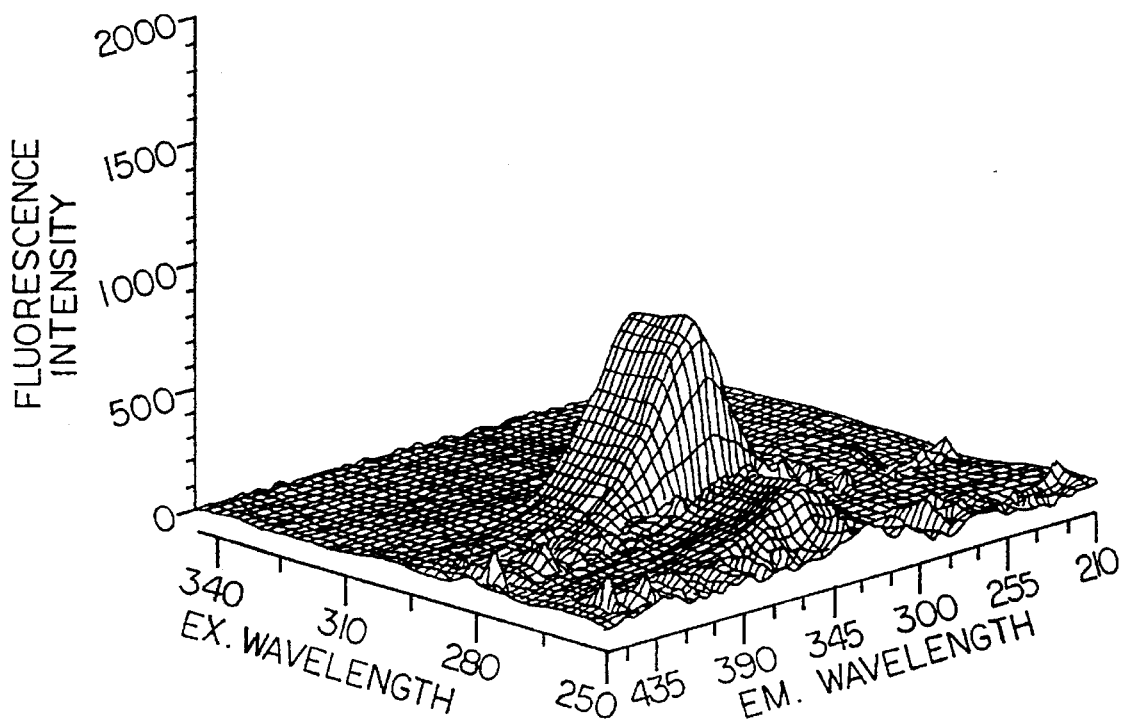
Figure 8D:
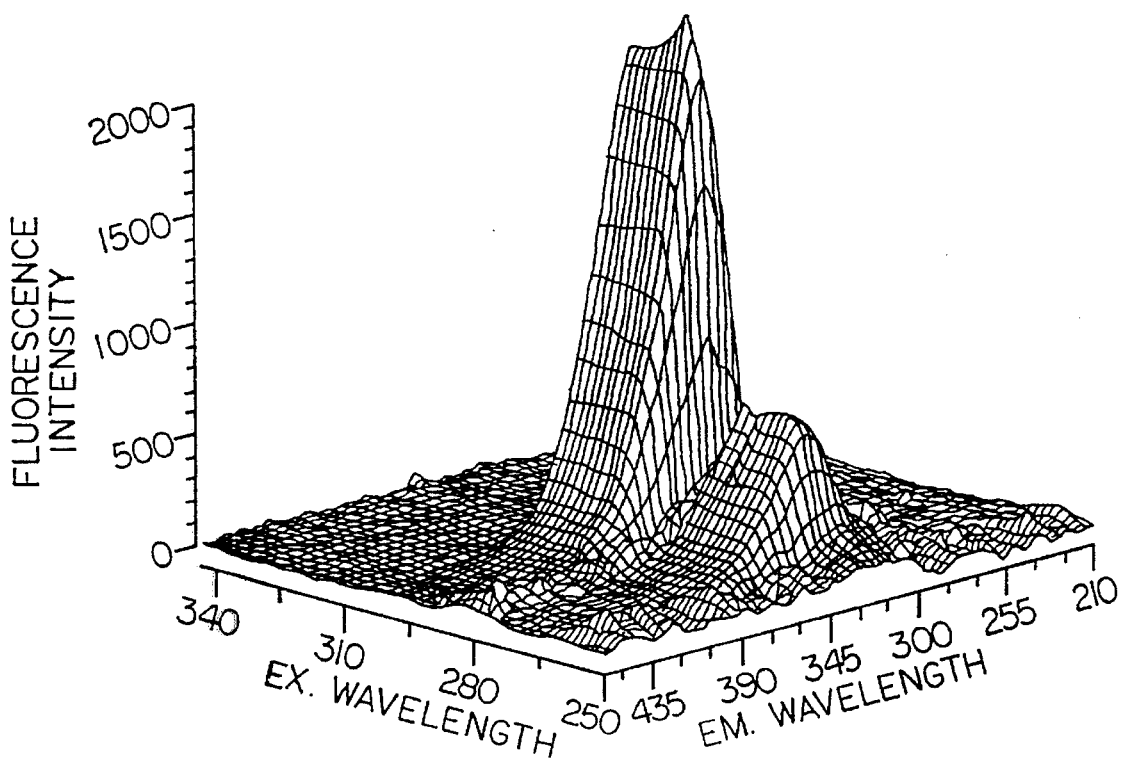

Referring now to FIG. 7, there is shown an enlarged fragmentary schematic section view of a third assembly or probe interchangeable with portion 81 for use with system 11, the assembly being represented generally by reference numeral 400.

Assembly or probe 400 is designed for use in analyzing solids, slurries or colloidal samples, such as found in soils or biological materials. A solid or liquid sample is placed against the outside of a rectangular sapphire window 415 installed into the side of a cylindrical housing 403. Excitation laser light is transported through optical fibers 437-1 through 437-n. The fibers are preferably polished at a 45 degree angle so that the laser beams are reflected by total internal reflection through one side of the fibers. The beams 440-1 through 440-n are then focused by lenses 412-1 through 412-n, respectively, onto the sample. Returning fluorescence and scattered light is focused by lenses 412-1 through 412-n onto the collection optical fibers (located beside optical fibers 437-1 through 437-n and hidden in FIG. 7). Room is available between the fibers and the lenses to insert additional optical elements such as additional lenses to manipulate the beam profile or filters to remove unwanted spectral regions. Absorption measurements, in the form of attenuated total reflection spectra, could be obtained in this type of probe by mounting a sapphire or diamond total internal reflection element into one side of the probe housing.

Assembly 400 can have a handle for hand dipping into solids/solutions, or can be attached to a machine designed to insert probes into solids or solutions. The sapphire window is resistant to chemicals and abrasion. An assembly as described above could be attached to the hydraulic ram of a cone penetrometer soil analysis system. By using long optical fibers, a probe of this type can be inserted into subsurface soil to a depth of 50 meters or more. If this probe is inserted into the sample at a rate such that the probe moves a distance equivalent to the distance between the optical fiber sampling regions between each exposure, then EEM's from the same point in space can be reconstructed from a series of consecutive exposures. The compact design of this probe permits all optical components to fit into a tube of less than ⅝ inch in diameter.

Referring now to FIGS. 8(*a*) through 8(*d*), there are shown respective ten-second exposure, excitation-emission matrices (EEM's) for static solutions of (a) 1000 ppm unleaded gasoline in water; (b) 100 ppm humic acid in water; (c) 1235 ppm aroclor 1262 in acetonitrile; and (d) 1167 ppm aroclor 1016 in acetonitrile. Each of these EEM's was obtained by substituting assembly 300 for portion 81 in system 11, with fibers 337 and 345 of assembly 300 being inserted into stationary solutions, the system being configured for ten excitation wavelengths, with ten excitation wavelengths and 150 emission wavelengths being gridded for continuity by a plotting program after spectral intensities were corrected for background solvent fluorescence and scattering.

The EEM of FIG. 8(*a*) indicates that the gasoline did not dissolve completely in the water. As can be seen by a review of FIGS. 8(*a*) through 8(*d*), the four chemical compounds exhibited different EEM's, which differences could be used to distinguish the four compounds for identification purposes.

Figure 9:
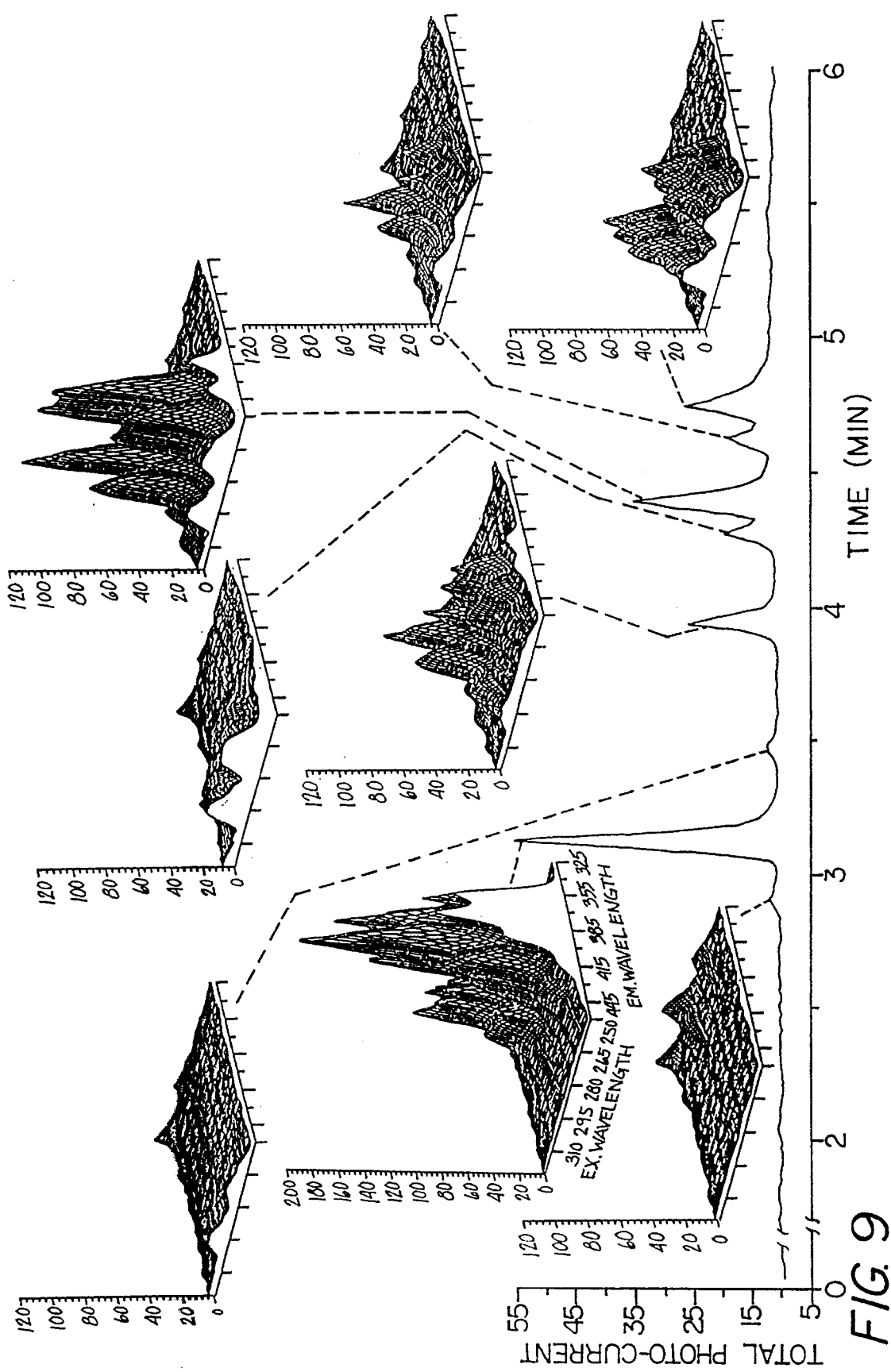
FIG. 9 shows a fluorescence chromatogram and selected EEM's for an 8-component mixture of polycyclic aromatic hydrocarbons obtained using the system of FIG. 1.
Figure 10A:
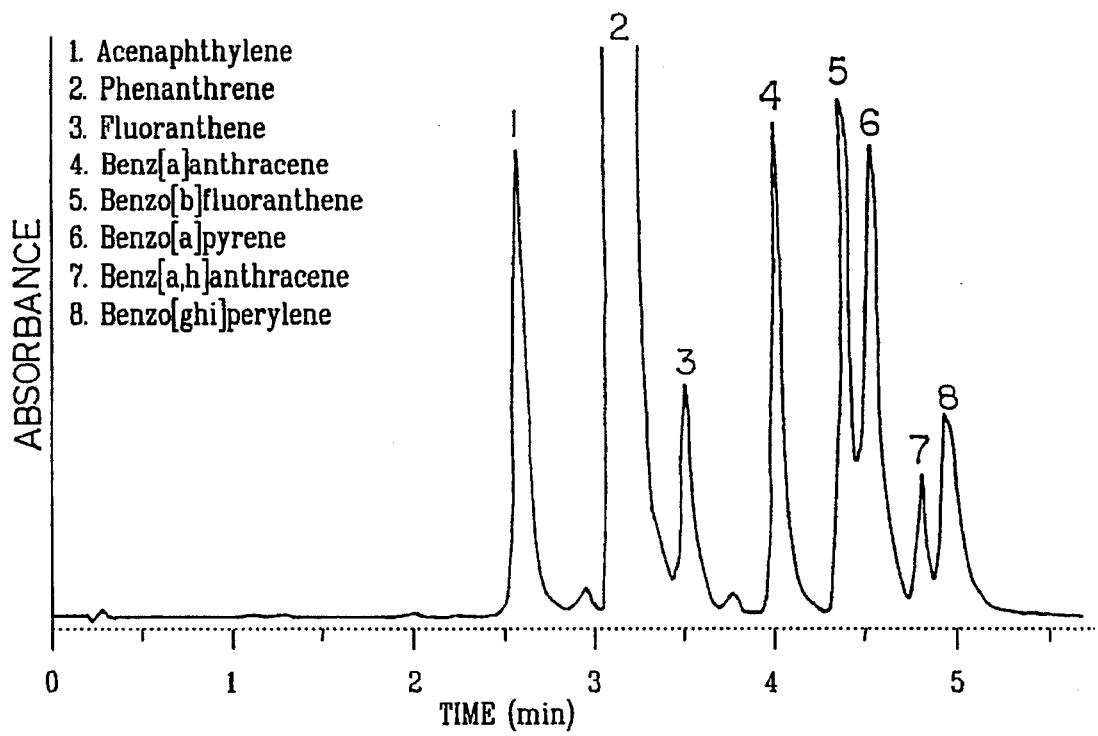
FIG. 10(a) is an absorption chromatogram for the same 8-component mixture tested in FIG. 9 obtained using a commercially available system.
Figure 10B:
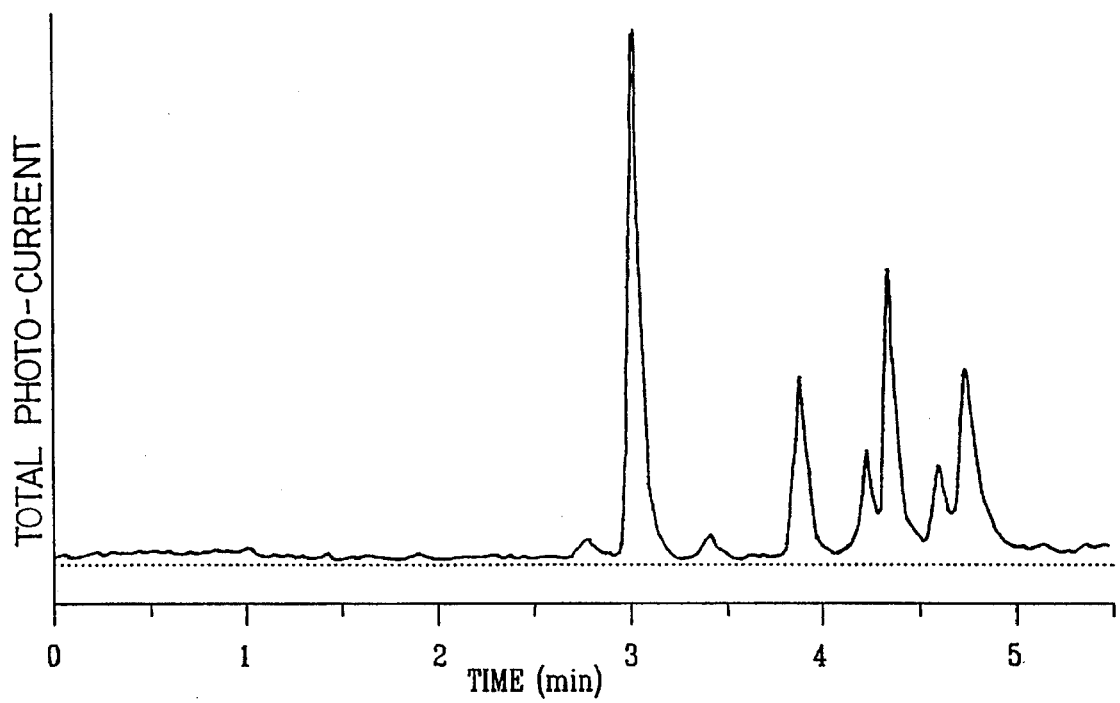
FIG. 10(b) is a fluorescence chromatogram for the same 8-component mixture tested in FIG. 10(a) obtained using the system of FIG. 1.
Figure 11:
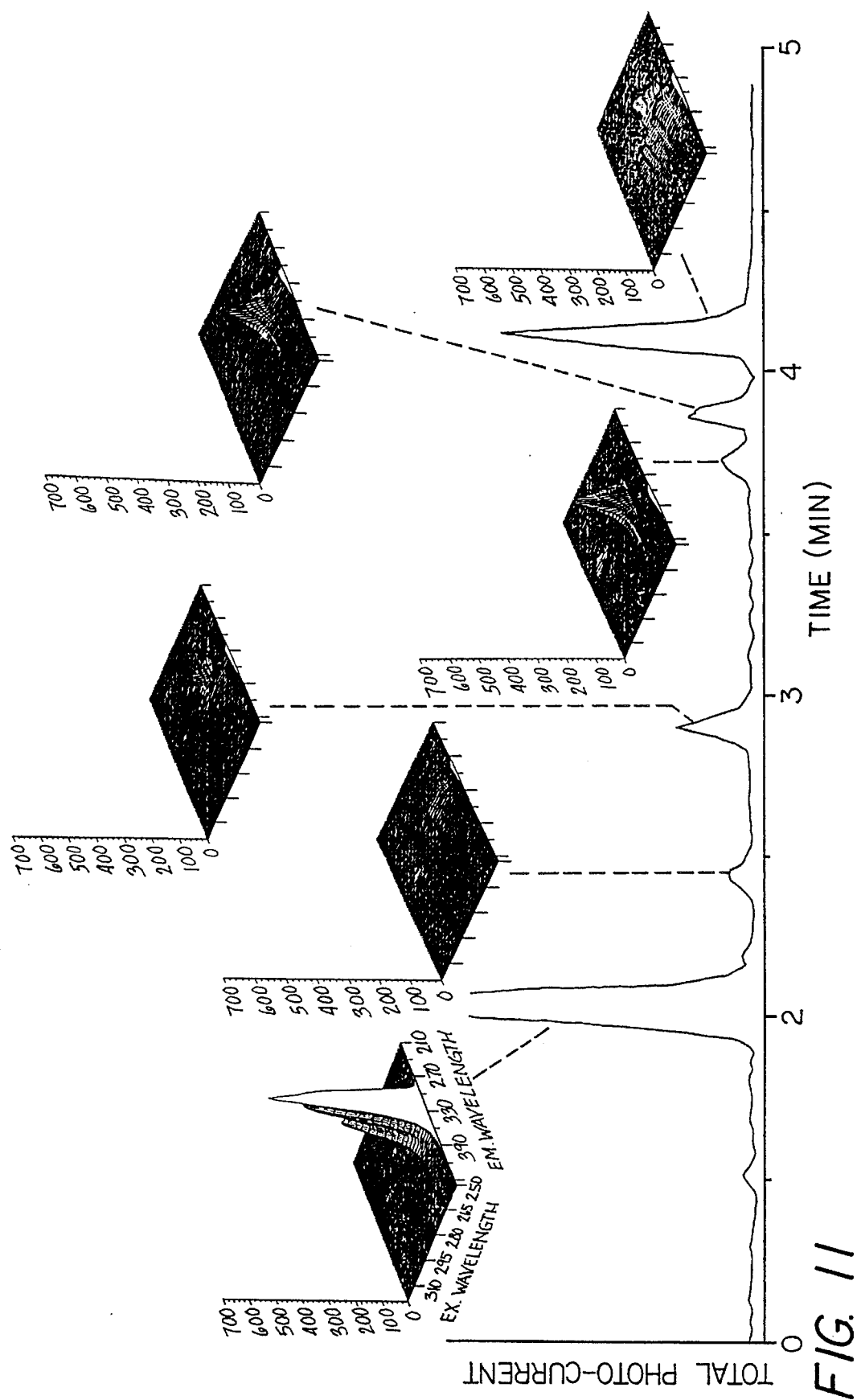
FIG. 11 shows a fluorescence chromatogram and selected EEM's of a 6-component mixture of aromatic pollutant chemicals obtained using the system of FIG. 1.

Referring now to FIGS. 9, 10(b) and 11, there are shown a series of chromatograms obtained using system 11 in conjunction with High Performance Liquid Chromatography (HPLC). The following chromatographic conditions were employed in all instances: 20 μL injection volume, $C_{18}$ on 0.3 μm spherical particle stationary phase, 4 ml/min flow rate, linear gradient elution starting with 35% acetonitrile in water to 100% acetonitrile over 5 minutes.

FIG. 9 shows the chromatogram and EEM's obtained on an 8-component mixture of polycyclic aromatic hydrocarbons (PAH's). The graph plots total photocurrent (i.e., total integrated fluorescence intensity at all excitation and emission wavelengths) against time. A total of 200 CCD exposures were taken sequentially, corrected for scattered light using a blank chromatogram, spectrally corrected, power normalized, integrated and plotted against time to generate the chromatogram. Each CCD exposure was integrated over 1.5 s and an additional 0.3 s per exposure was required for readout. The EEM's shown in FIG. 9 are the 1.5 s exposure EEM's observed at the chromatographic peaks. The excitation wavelengths, emission wavelengths and intensity scales of the EEM's are the same for all EEM's. As can be seen, the EEM's of a chemical are very characteristic of that chemical. Therefore, the EEM's can be used to identify unknown chemicals when mixtures containing unknown chemicals are chromatographed for chemical analysis.

FIGS. 10(a) and 10(b) contrast the absorption chromatogram obtained with a commercially available detector (Perkin-Elmer 235 detector set at 255 nm, 8 μl detection cell volume) with the fluorescence chromatogram obtained using system 11. The 8 PAH compounds of the mixture, the same mixture as used to generate the chromatogram of FIG. 9, are numbered in the order of elution in FIG. 10(a). All peaks in the absorption chromatogram appear in the EEM fluorescence chromatogram (except acenaphthylene, which is non-fluorescent), and all peaks have the same retention times and widths. This demonstrates that system 11 obtains data of the same quality as that of a commercially available instrument. The concentrations of the compounds in this mixture were about 8–30 ppm.

FIG. 11 shows the chromatogram and EEM's of a 6-component mixture of aromatic pollutant chemicals. The chemicals in this chromatogram and their original concentrations in the order of elution are: p-xylene (540 ppm); styrene (132 ppm); 2-methylnaphthalene (54 ppm); 9-methylfluorene (18 ppm); p-terphyenyl (17 ppm); and 2-methylphenanthrene (12 ppm).

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims. For example, one or more of the spectral channels of the above-described system could be used to measure any phenomenon, other than absorption or laser-induced-fluorescence, that produces an electromagnetic (light) signal within the wavelength range of the spectrograph and the detector. Examples of such phenomena include Resonance Raman, surface enhanced Raman, ultrasonic induced luminescence (sonoluminescence), atomic or molecular emission induced in a flame or ionic plasma, and optical chemical reaction systems. Optical chemical reaction system are any reactions systems that employ chemical reactions to improve the optical detectability of chemicals which one desires to detect. The number of discrete spectral channels of optical information that can be processed at one time depends on (1) the size of optical fibers employed; (2) the quality of the imaging spectrograph and the detector (interchannel optical and pixel crosstalk); and (3) the 2-dimensional detector's active area and pixel size.

In addition to the spectrally-dispersed channels of system 11, one could add additional undispersed detection channels that are acquired at exactly the same time that the dispersed channels are acquired. These channels would preferably be located in a region of the CCD detector that is currently not used in system 11, for instance, in the regions of each spectral channel that are of higher energy than the laser wavelength employed for fluorescence excitation in that channel. The polychromator housing would have to be modified slightly in order to allow the light from these separate channels to be imaged directly onto the surface of the CCD in the proper location. Spectral selection in these channels could be accomplished with optical elements separate from the polychromator currently used in system 11. It is estimated that at least 10 of these channels could be introduced into system 11 (having less than $10^{-4}$ crosstalk between channels). Also, one of the existing spectral channels could be sacrificed to allow an entire row of these undispersed channels to be introduced into the system. This would add an additional 20 undispersed detection channels to the system.

One could also program the CCD detector to obtain different information in alternate exposures using the current detector instrumentation. For instance, after the CCD detection system acquires the usual number of spectral channels (e.g. 13), the detector can be programmed to acquire 26 additional spectral channels positioned between the usual 13 channels in 2 subsequent exposures. This can be done, for example, if each active optical fiber (carrying light) is separated from each adjacent active optical fiber by two inactive optical fibers (carrying no light). These inactive fibers could be attached to optical sensors and used in alternate exposures in the acquisition of as many as 39 separate optical spectral channels without any sacrifice in interchannel crosstalk. This mode of operation would likely require shutters and computer timing routines to coordinate the selection of active optical fibers with the data collection procedure.

What is claimed is:

1. A method for examining the composition of a fluid or solid sample, said method comprising the steps of:

a) simultaneously illuminating the fluid or solid sample with a plurality of laser pulses of different wavelengths, each laser pulse illuminating a spatially discrete portion of the fluid or solid sample; and b) detecting the resultant fluorescence simultaneously emitted from each of the illuminated spatially discrete portions of the fluid or solid sample.

2. The method as claimed in claim 1 wherein at least one of said plurality of laser pulses is in the ultraviolet region of the spectrum.

3. The method as claimed in claim 1 wherein two or more of said plurality of laser pulses are in the ultraviolet region of the spectrum.

4. The method as claimed in claim 1 wherein the fluid or solid sample is an effluent sample and wherein each of the spatially discrete illuminated portions of the effluent sample lie along the same point of axial flow.

5. A method for examining the composition of a fluid or solid sample, said method comprising the steps of:

a) simultaneously illuminating the fluid or solid sample with a plurality of laser pulses of different wavelengths, each laser pulse illuminating a spatially discrete portion of the fluid or solid sample;

b) detecting the resultant fluorescence simultaneously emitted from each of the illuminated spatially discrete portions of the fluid or solid sample;

c) illuminating with lamp light a portion of the fluid or solid sample not simultaneously illuminated by one of said plurality of laser pulses; and d) measuring the amount of light from said lamp absorbed by the fluid or solid sample.

6. The method as claimed in claim 5 wherein said lamp light emits in at least a portion of the spectral region of approximately 200–470 nm.

7. A method of examining the composition of a sample, said method comprising the steps of:

a) illuminating a first spatial region of the sample with light of a suitable fluorescence excitation wavelength;

b) simultaneously thereto, illuminating a second spatial region of the sample with light of one or more suitable absorption wavelengths, said first and said second spatial regions being discrete; and c) detecting the resultant fluorescence and absorption from said first and said second spatial regions, respectively, of the sample.

8. The method as claimed in claim 7 wherein said sample is a fluid sample.

9. A system for use in examining the composition of a fluid or solid sample, said system comprising:

a) means for holding the fluid or solid sample;

b) means for simultaneously generating a plurality of laser pulses of different wavelengths emitted along a common axis;

c) means for dispersing said laser pulses according to their respective wavelengths along non-intersecting paths;

d) a first plurality of optic fibers, each of said first plurality of optic fibers being used to transmit one of said plurality of dispersed laser pulses to a spatially discrete portion of the fluid or solid sample;

e) a second plurality of optic fibers, each of said second plurality of optic fibers being arranged to receive fluorescence from a corresponding spatially discrete illuminated portion of the fluid or solid sample;

f) an imaging spectrograph for spectrally resolving the fluorescence transmitted by each of said second plurality of optic fibers; and g) a CCD detector for detecting the output of said imaging spectrograph.

10. The system as claimed in claim 9 wherein each of said first plurality of optical fibers and said second plurality of optical fibers are connectorized.

11. The system as claimed in claim 9 wherein said means for simultaneously generating a plurality of laser pulses of different wavelengths comprises a Raman shifter.

12. The system as claimed in claim 9 wherein said means for simultaneously generating a plurality of laser pulses of different wavelengths comprises a pulsed Nd:YAG laser, a harmonic generator coupled to the output of said Nd:YAG laser for generating a family of harmonics for said pulsed Nd:YAG laser, means for selecting out from said family of harmonics the fourth harmonic of said pulsed Nd:YAG laser and a Raman shifter optically coupled to the output of said selecting means, said Raman shifter containing a mixture of hydrogen and methane gases capable of generating at least about 10 different-colored UV laser pulses.

13. The system as claimed in claim 9 further comprising a computer for processing the output of said CCD detector and for generating excitation-emission-matrices.

14. The system as claimed in claim 9 further comprising a lamp source for illuminating a portion of the fluid sample not simultaneously illuminated by one of said plurality of laser pulses and optic fiber means for conveying the light transmitted through the fluid sample to said imaging spectrograph.

15. The system as claimed in claim 14 wherein said lamp source comprises means for emitting light over the spectral region of about 200–470 nm.

16. The system as claimed in claim 14 wherein said lamp source includes an arrangement of deuterium, xenon and/or tungsten filament lamps.

17. The system as claimed in claim 9 wherein said holding means comprises a cell which includes a fluid inlet and a fluid outlet, said fluid inlet and said fluid outlet being in fluid communication with one another, and wherein said system further comprises means for conducting a flow of fluid to said fluid inlet and means for conducting a flow of fluid away from said fluid outlet so as to create a fluid flow between said fluid inlet and said fluid outlet within said cell for use in examining effluent fluid samples.

18. The system as claimed in claim 17 wherein said first plurality of optic fibers are arranged to illuminate spatially discrete portions of the fluid sample at the same axial point of fluid flow.

19. The system as claimed in claim 18 wherein said cell is shaped to include a lower chamber adapted for absorption measurements and an upper chamber adapted for fluorescence measurements.

20. A system for use in examining the composition of a fluid or solid sample, said system comprising:

a) means for holding the fluid or solid sample;

b) means for simultaneously illuminating the fluid or solid sample with light of a plurality of suitable fluorescence excitation wavelengths, the light of each fluorescence excitation wavelength illuminating a spatially discrete portion of the fluid or solid sample;

c) means for detecting the resultant fluorescence emitted from each of the illuminated spatially discrete portions;

d) means for illuminating a portion of the fluid or solid sample not contemporaneously illuminated with light of a suitable excitation wavelength with light of one or more suitable absorption wavelengths; and e) means for detecting the amount of light absorbed by the portion of the fluid or solid sample illuminated with light of said one or more suitable absorption wavelengths.

21. The system as claimed in claim 20 wherein said means for simultaneously illuminating the fluid or solid sample with light of a plurality of suitable fluorescence excitation wavelengths comprises a lamp and means for dispersing the light emitted from said lamp according to its constituent wavelengths and wherein said means for illuminating the fluid or solid sample with light of one or more suitable absorption wavelengths comprises said lamp.

22. A system for use in examining the composition of a fluid or solid sample, said system comprising:

a) means for holding the fluid or solid sample;

b) means for simultaneously generating a plurality of laser pulses of different wavelengths emitted along a common axis;

c) means for dispersing said laser pulses according to their respective wavelengths along non-intersecting paths;

d) a first plurality of optic fibers, each of said first plurality of optic fibers being used to transmit one of said plurality of dispersed laser pulses to a spatially discrete portion of the fluid or solid sample;

e) a second plurality of optic fibers, each of said second plurality of optic fibers being arranged to receive fluorescence from a corresponding spatially discrete illuminated portion of the fluid or solid sample;

f) an imaging spectrograph for spectrally resolving the fluorescence transmitted by each of said second plurality of optic fibers; and g) detector means for detecting the output of said imaging spectrograph.

23. The system as claimed in claim 22 wherein said means for simultaneously generating a plurality of laser pulses of different wavelengths comprises means for emitting UV light.

24. The system as claimed in claim 22 wherein said means for simultaneously generating a plurality of laser pulses of different wavelengths comprises a pulsed Nd:YAG laser, a harmonic generator coupled to the output of said Nd:YAG laser for generating a family of harmonics for said pulses Nd:YAG laser, means for selecting out from said family of harmonics a suitable harmonic of said pulsed Nd:YAG laser, and a Raman shifter optically coupled to the output of said selecting means, said Raman shifter containing a mixture of hydrogen and methane gases capable of generating at least about 10 different-colored UV laser pulses.

25. The system as claimed in claim 22 further comprising a computer for processing the output of said detector means and for generating excitation-emission-matrices.

* * * * *